(12) United States Patent
Haratani et al.

(10) Patent No.: US 10,948,395 B2
(45) Date of Patent: Mar. 16, 2021

(54) BIOSENSOR AND BIOCHIP

(71) Applicant: TDK CORPORATION, Tokyo (JP)

(72) Inventors: Susumu Haratani, Tokyo (JP); Sachio Tsuboike, Tokyo (JP); Sumiko Kitagawa, Tokyo (JP); Takashi Kikukawa, Tokyo (JP); Haruki Yuga, Tokyo (JP)

(73) Assignee: TDK CORPORATION, Tokyo (JP)

( * ) Notice: Subject to any disclaimer, the term of this patent is extended or adjusted under 35 U.S.C. 154(b) by 163 days.

(21) Appl. No.: 16/089,122

(22) PCT Filed: Mar. 24, 2017

(86) PCT No.: PCT/JP2017/012027
§ 371 (c)(1),
(2) Date: Sep. 27, 2018

(87) PCT Pub. No.: WO2017/170230
PCT Pub. Date: Oct. 5, 2017

(65) Prior Publication Data
US 2019/0064046 A1 Feb. 28, 2019

(30) Foreign Application Priority Data

Mar. 28, 2016 (JP) .............................. JP2016-063490
May 25, 2016 (JP) .............................. JP2016-104468

(51) Int. Cl.
*G01N 15/06* (2006.01)
*G01N 33/543* (2006.01)
(Continued)

(52) U.S. Cl.
CPC ..... *G01N 15/0656* (2013.01); *G01N 15/0606* (2013.01); *G01N 27/745* (2013.01);
(Continued)

(58) Field of Classification Search
CPC .......... G01N 15/0656; G01N 15/0606; G01N 27/745; G01N 33/54386; G01N 2015/0065
See application file for complete search history.

(56) References Cited

U.S. PATENT DOCUMENTS 8,183,058 B2 * 5/2012 Hatakeyama .... G01N 33/54386
422/408
2005/0087000 A1 4/2005 Coehoorn et al.
(Continued)

FOREIGN PATENT DOCUMENTS

JP 2005-513475 A 5/2005
JP 2007-278966 A 10/2007
(Continued)

OTHER PUBLICATIONS

Jun. 6, 2017 International Search Report issued in International Patent Application No. PCT/JP2017/012027.
(Continued)

*Primary Examiner* — Tung X Nguyen
*Assistant Examiner* — Feba Pothen
(74) *Attorney, Agent, or Firm* — Oliff PLC (57) ABSTRACT

What provided is a biosensor including: a substrate having a surface with first and second regions adjacent each other; a magnetoresistance effect element disposed on the first region; a soft magnetic thin film on the second region; a protective film disposed on both the first region and the second region, covering a surface of the soft magnetic thin film, and disposed on the top part of the second region and contains an affinity substance recognizing the biomolecule on the outer surface of the second region exclusively; and an MR cover film disposed on at least the top part of the first region, disposed on the protective film above the magnetoresistance effect element, and being free of the affinity substance, wherein the soft magnetic thin film transmits an
(Continued)

in-plane component of a stray magnetic field of magnetic beads to the magnetoresistance effect element.

16 Claims, 7 Drawing Sheets

(51) Int. Cl.
  *G01N 27/74* (2006.01)
  *G01N 15/00* (2006.01)
(52) U.S. Cl.
  CPC .............. *G01N 33/54386* (2013.01); *G01N 2015/0065* (2013.01)

(56) References Cited

U.S. PATENT DOCUMENTS

| | | |
|---|---|---|
| 2007/0237673 A1 | 10/2007 | Ikeda et al. |
| 2008/0014651 A1 | 1/2008 | Bangert |
| 2008/0032423 A1 | 2/2008 | Wang et al. |
| 2009/0000360 A1 | 1/2009 | Ogawa et al. |
| 2009/0243594 A1 | 10/2009 | Kahlman |
| 2010/0167263 A1* | 7/2010 | Groll ................ G01N 33/54393 435/4 |
| 2011/0156702 A1 | 6/2011 | Kim et al. |
| 2015/0044778 A1 | 2/2015 | Wang et al. |
| 2019/0003956 A1 | 1/2019 | Campidelli et al. |

FOREIGN PATENT DOCUMENTS

| | | |
|---|---|---|
| JP | 2008-039782 A | 2/2008 |
| JP | 2008-151761 A | 7/2008 |
| JP | 2009-002838 A | 1/2009 |
| JP | 2014-528071 A | 10/2014 |

OTHER PUBLICATIONS

Jun. 6, 2017 International Search Report issued in International Patent Application No. PCT/JP2017/012043.
Jun. 6, 2017 International Search Report issued in International Patent Application No. PCT/JP2017/012041.
Dec. 9, 2020 Office Action issued in U.S. Appl. No. 16/088,988.
Dec. 9, 2020 Office Action issued in U.S. Appl. No. 16/089,007.

* cited by examiner

BIOSENSOR AND BIOCHIP

TECHNICAL FIELD

The present disclosure relates to a biosensor and a biochip.

Priority is claimed on Japanese Patent Application No. 2016-063490, filed Mar. 28, 2016, and Japanese Patent Application No. 2016-104468, filed May 25, 2016, the content of which is incorporated herein by reference.

BACKGROUND ART

As a magnetic sensor, a magnetoresistance effect element such as a giant magnetoresistive effect (GMR) element, a magnetic tunnel junction (TMR) element, and an anisotropic magnetoresistive effect (AMR) element is often used (for example, refer to Published Japanese Translation No. S/H 2005-513475 of the PCT International Publication). A magnetoresistance effect element is an element whose output resistance value changes according to an input magnetic field, and it is possible to measure a change in the detected magnetic field on the basis of the output resistance value.

Figure 5:
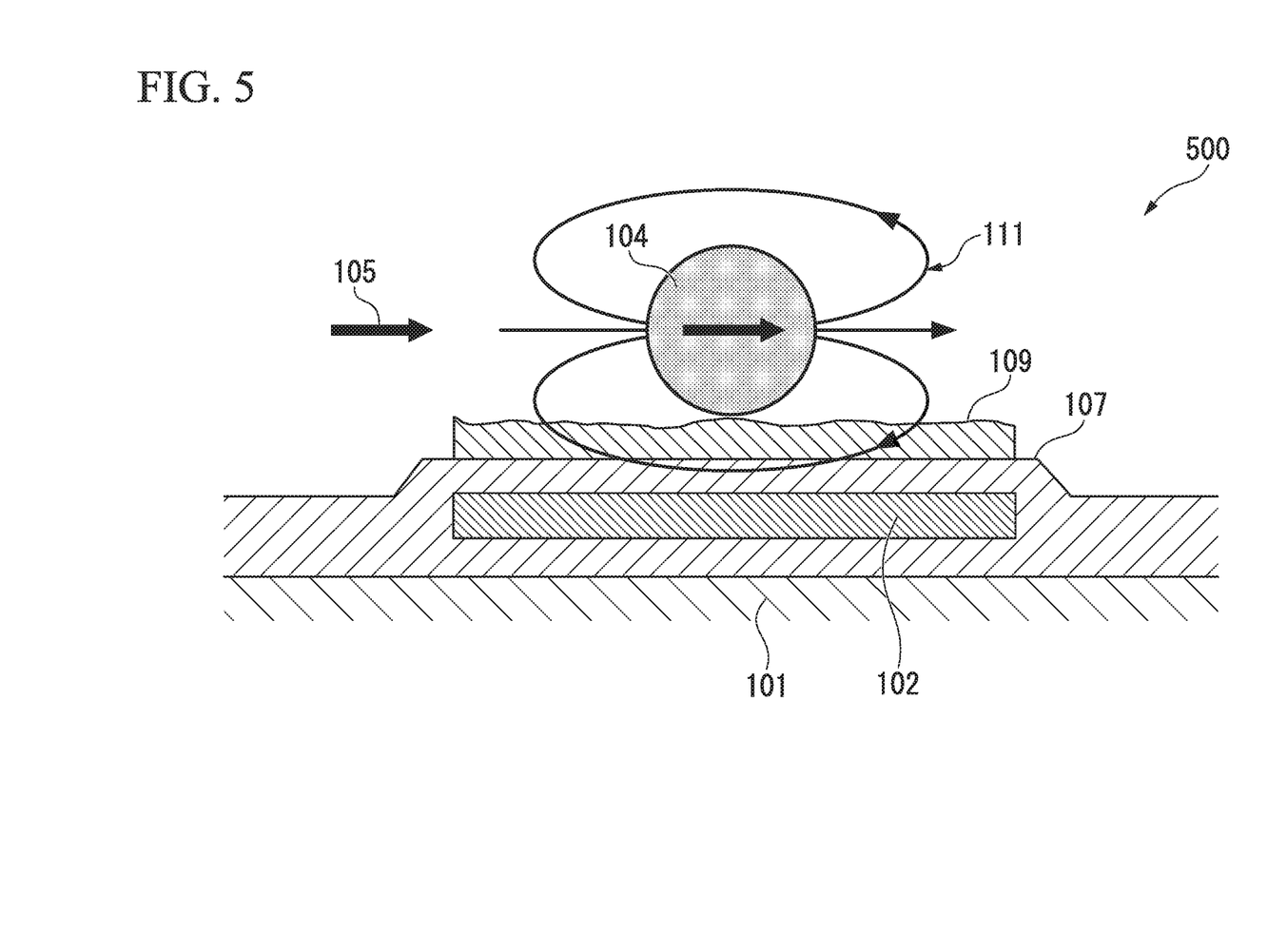
FIG. 5 is a cross-sectional view of a magnetic detection type biosensor of the related art.
Figure 6:
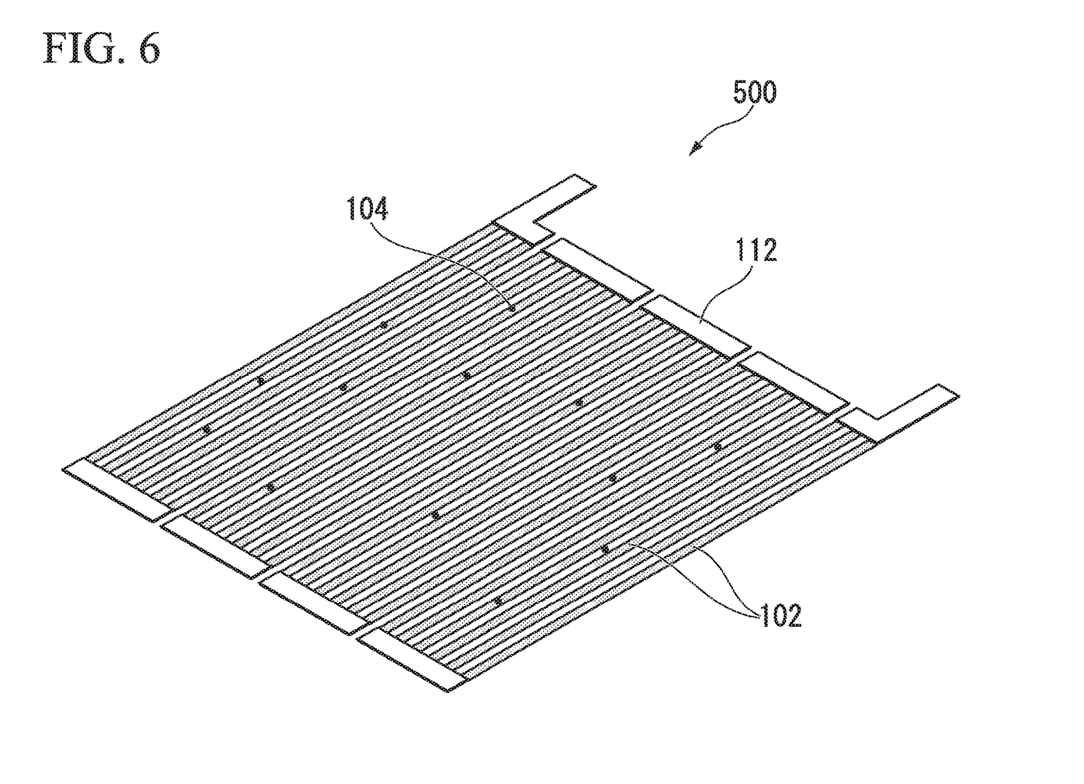
FIG. 6 is a perspective view of the magnetic detection type biosensor of the related art.

FIG. 5 and FIG. 6 are diagrams for explaining a biosensor 500 of the related art. As shown in FIG. 5, the biosensor 500 includes a substrate 101, a magnetoresistance effect element 102, a protective film 107, and a biomolecule capturing layer 109 that captures target biomolecules in that order. When biomolecules in a sample are captured on the biomolecule capturing layer 109, magnetic beads having affinity for the biomolecules are captured on the biomolecule capturing layer 109 via the biomolecules and a magnetic field is then horizontally applied (an applied magnetic field 105), a stray magnetic field 111 is generated from magnetic beads 104 and the stray magnetic field 111 is input to the magnetoresistance effect element 102.

FIG. 6 is a diagram showing details of the magnetoresistive element 102 of the related art used in the biosensor 500 of the related art. As shown in FIG. 6, the magnetoresistance effect element 102 has a meander structure with sets of three lines.

SUMMARY

Technical Problem

As shown in FIG. 5, in a biosensor 500 of the related art, since a direction in which an external magnetic field is applied matches a magnetic sensing direction of a magnetoresistance effect element 102, if an applied magnetic field 105 as an external magnetic field is strengthened in order to increase a stray magnetic field 111 from the magnetic beads 104, the magnetization of a magnetosensitive layer of a magnetoresistance effect element becomes saturated and there is a problem of a required output not being obtained.

As shown in FIG. 6, in the meander structure, there are cases in which the magnetic beads 104 are disposed on the magnetoresistance effect elements 102 and disposed between the magnetoresistance effect elements 102. Since the output varies according to a difference in the disposition, that is, a relative position between the magnetoresistance effect elements 102 and the magnetic beads 104, there are problems of measured values of a quantity or a concentration of magnetic beads varying and sufficient accuracy not being obtained.

In order to solve the above problems, the inventors have developed a biosensor through which it is possible to calculate the number of biomolecules contained in a sample, and it is possible to secure quantitation of biomolecules in a sample with high accuracy and high sensitivity.

Figure 7:
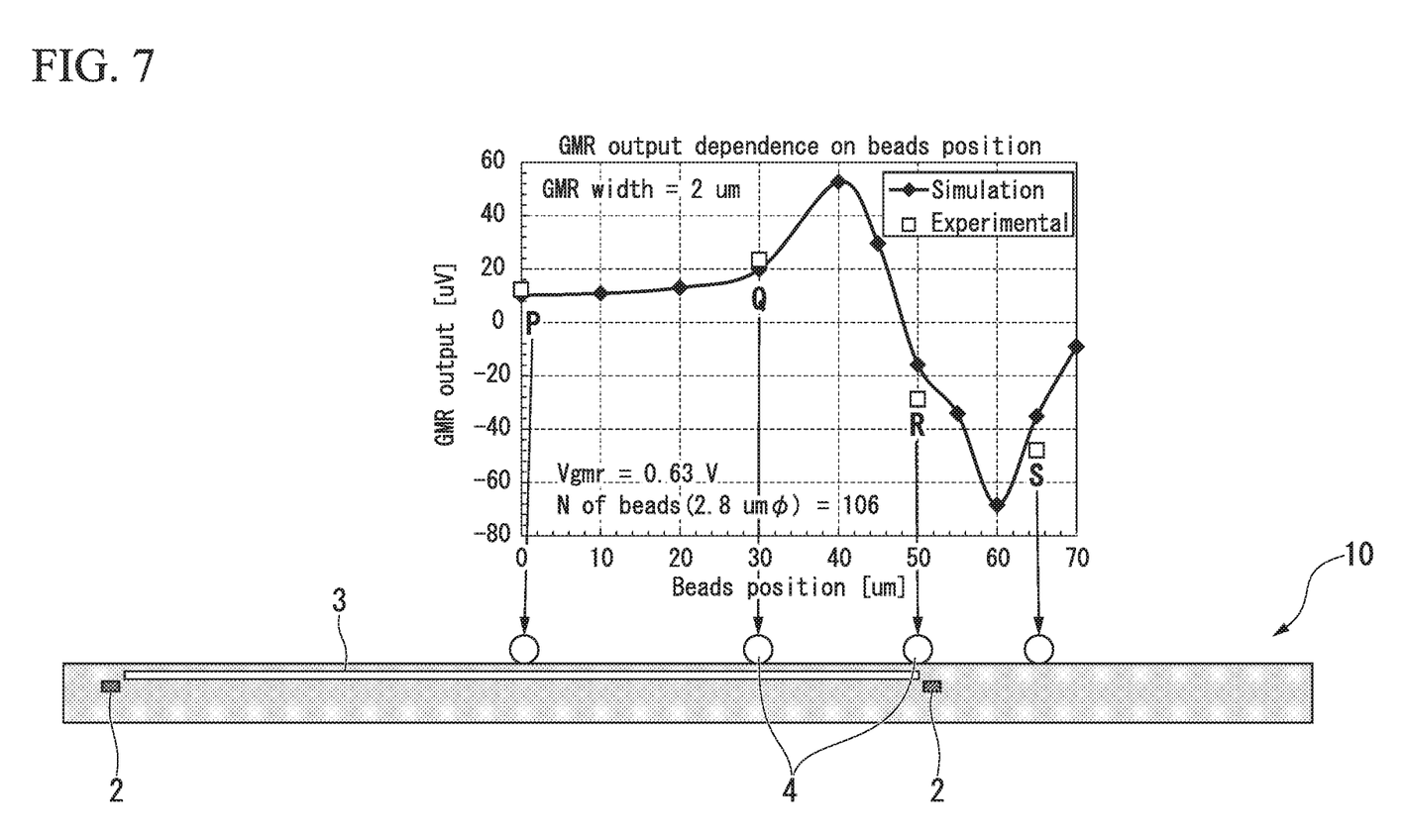
FIG. 7 shows a graph of results obtained by simulating GMR outputs according to positions of magnetic beads from measured values of GMR outputs at P, Q, R, and S points in the biosensor and shows a cross-sectional view of the biosensor in which P, Q, R, and S points which are positions of magnetic beads are represented.

FIG. 7 shows a graph of results obtained by simulating GMR outputs according to positions of magnetic beads from measured values of GMR outputs at P, Q, R, and S points in the biosensor developed by the inventors and shows a cross-sectional view of the biosensor in which P, Q, R, and S points which are positions of magnetic beads are represented. In the cross-sectional view of the biosensor shown in FIG. 7, the reference numeral 10 indicates a biosensor, the reference numeral 2 indicates a magnetoresistance effect element, the reference numeral 3 indicates a soft magnetic thin film, and the reference numeral 4 indicates a magnetic bead.

As shown in FIG. 7, GMR outputs vary according to positions of magnetic beads on the biosensor developed by the inventors, which is a problem.

The present disclosure has been made in view of the above circumstances and provides a biosensor that reduces variation in GMR outputs and detects biomolecules in a sample with high accuracy and high sensitivity.

Solution to Problem

The inventors conducted extensive studies in order to address the above problem, and as a result, found that, when a cover film is disposed above a magnetoresistance effect element, it is possible to reduce variation in GMR outputs, and thereby completed the present disclosure.

That is, the present disclosure is directed to the following aspect.

A biosensor for detecting a biomolecule in a sample, the biosensor including:

a substrate having a surface in which a first region and a second region disposed adjacent to the first region are formed;

a magnetoresistance effect element that is disposed on the first region and is configured for a detected resistance value to be changed based on an input magnetic field;

a soft magnetic thin film that is disposed on the second region;

a protective film that is disposed on both the first region and the second region, covers a surface of the soft magnetic thin film, is disposed on a top part of the second region and contains an affinity substance capable of recognizing the biomolecule on the outer surface of the second region exclusively; and an MR cover film that is disposed on at least the top part of the first region, is disposed on the protective film above the magnetoresistance effect element, and is substantially free of the affinity substance, wherein the soft magnetic thin film is configured to transmit a component in an in-plane direction of a laminate of a stray magnetic field of magnetic beads accumulated on the soft magnetic thin film to the magnetoresistance effect element, and the protective film and the MR cover film are made of different materials.

DESCRIPTION OF EMBODIMENTS

◇ Biosensor

A biosensor according to an embodiment of the present disclosure includes a substrate, a magnetoresistance effect element, a protective film, and an MR cover film.

The substrate has a surface in which a first region and a second region disposed adjacent to the first region are formed.

The magnetoresistance effect element is disposed on the first region and is configured for a detected resistance value to be changed based on an input magnetic field.

The soft magnetic thin film is disposed on the second region and is configured to transmit a component in the in-plane direction of the laminate of a stray magnetic field of magnetic beads accumulated on the soft magnetic thin film to the magnetoresistance effect element.

The protective film is disposed on both the first region and the second region, covers a surface of the soft magnetic thin film, and is disposed on the top part of the second region, and contains an affinity substance capable of recognizing the biomolecule on the outer surface of the second region exclusively.

The MR cover film is disposed on at least the top part of the first region and is disposed on the protective film above the magnetoresistance effect element, and is substantially free of the affinity substance.

The protective film and the MR cover film are made of different materials.

According to the biosensor of the present disclosure, variation in GMR outputs is reduced and it is possible to detect biomolecules in a sample with high accuracy and high sensitivity.

Here, in this specification, the "biosensor" refers to a sensor that detects biological materials (that may be naturally derived or chemically synthesized) such as enzymes, antigens, antibodies, and nucleic acids (including not only DNA, RNA, and the like but also artificial nucleic acids, for example, LNA).

In addition, the "MR cover film" refers to a film for protecting a magnetoresistance effect element.

When the biosensor of the present embodiment includes the MR cover film that is substantially free of an affinity substance, variation in GMR outputs is reduced and it is possible to detect biomolecules in a sample with high accuracy and high sensitivity.

In this specification, "substantially free of an affinity substance" refers to a case in which no affinity substance is contained or a case in which, for example, when an affinity substance is nonspecifically adsorbed onto an MR cover film, the affinity substance is contained only in an amount at which it is not possible to capture biomolecules.

© Structure of Biosensor

Differences in structures of biosensors of the present embodiment will be described below with reference to the drawings. Here, in the drawings used in the following descriptions, in order to facilitate understanding of features of the present disclosure, feature parts are enlarged for convenience of illustration in some cases, and dimensional proportions and the like of components are not necessarily the same as those of actual components.

First Embodiment

Figure 1:
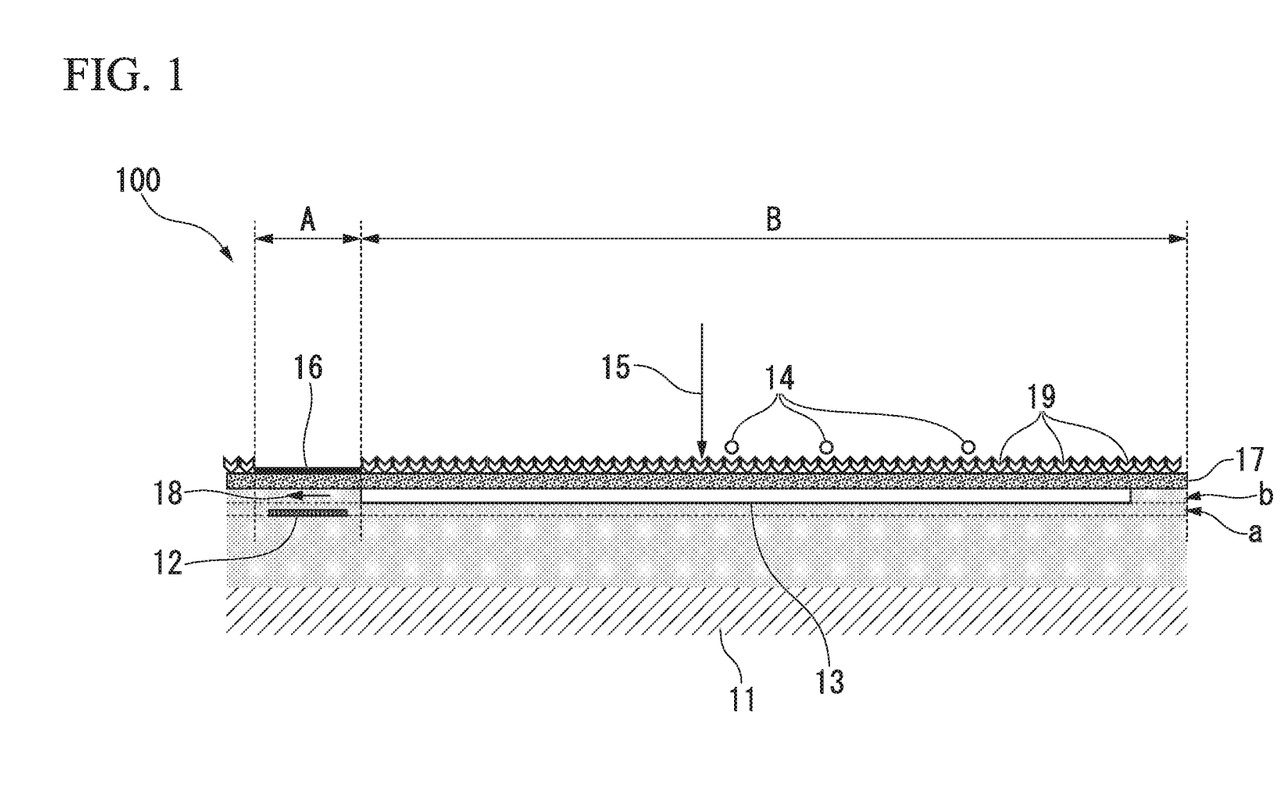
FIG. 1 is a cross-sectional view schematically showing a biosensor according to a first embodiment of the present disclosure.

FIG. 1 is a cross-sectional view schematically showing a biosensor according to a first embodiment of the present disclosure.

A first region, a second region, a first plane, a second plane, a third plane, and a fourth plane, which will be described below, are introduced for convenience in order to define a positional relationship between members on an area or plane in a virtual area or plane. Here, on the bio sensor of the embodiment to be described below, the first region and the second region are alternately repeatedly provided, and in a biosensor 100 shown in FIG. 1, one among a plurality of first regions and second regions is extracted and shown.

The biosensor 100 of the present embodiment detects biomolecules in a sample.

The substrate 11 has a first region A and a second region B on its surface. The magnetoresistance effect element 12 is disposed on the first region A and is configured for a detected resistance value to be changed based on an input magnetic field. A magnetic thin film 13 is disposed on the second region B. The protective film 17 is disposed on both the first region A and the second region B and covers a surface of the soft magnetic thin film 13. In addition, the protective film 17 contains an affinity substance (first affinity substance) 19. The affinity substance 19 allows recognition of biomolecules on the outer surface of the second region exclusively B. The MR cover film 16 is disposed on at least the top part of the first region A and is disposed on the protective film 17 above the magnetoresistance effect element 12 and is substantially free of the affinity substance 19.

Thus, it is possible to reduce adsorption of biomolecules or magnetic beads 14 on an MR cover layer, variation in GMR outputs is reduced, and it is possible to detect biomolecules in a sample with high accuracy and high sensitivity.

In addition, in the present embodiment, the magnetic beads 14 contain a second affinity substance (not shown) that allows recognition of a part that is different from the biomolecule recognition part of the first affinity substance 19. The magnetic beads 14 accumulate on the protective film 17 via a first affinity substance-biomolecule-second affinity substance complex, and when a magnetic field (an applied magnetic field 15) is applied in a direction crossing the soft magnetic thin film 13, a detection magnetic field 18 (leakage magnetic field) is input to the magnetoresistance effect element 12.

As shown in FIG. 1, the magnetoresistance effect element 12 is disposed on a first plane a which is positioned away from the main surface of the substrate 11 and is substantially parallel to the main surface of the substrate 11. In addition, the soft magnetic thin film 13 is disposed on a second plane b which is positioned further away from the main surface of the substrate 11 than the first plane a. That is, in the present embodiment, the main surface of a magnetoresistance effect element 2 that faces the substrate 11 and the main surface of the soft magnetic thin film 13 that faces the substrate 1 are disposed at different positions in the normal direction with respect to the substrate 11.

The surface of the soft magnetic thin film 13 is covered with the protective film 17 and the outer surface of the protective film 17 contains the first affinity substance 19 that captures biomolecules to be detected. The magnetic beads 14 also contain a second affinity substance (not shown) that captures biomolecules. The first affinity substance 19 and the second affinity substance allow recognition of different parts in biomolecules. That is, they can form a first affinity substance-biomolecule-second affinity substance complex.

In addition, on a third plane (not shown) that is positioned further away from the main surface of the substrate 1 than the first plane and the second plane, an electrode terminal (not shown) is disposed. The electrode terminal is connected to the magnetoresistance effect element 12 via an internal wiring (not shown).

Second Embodiment

Figure 2:
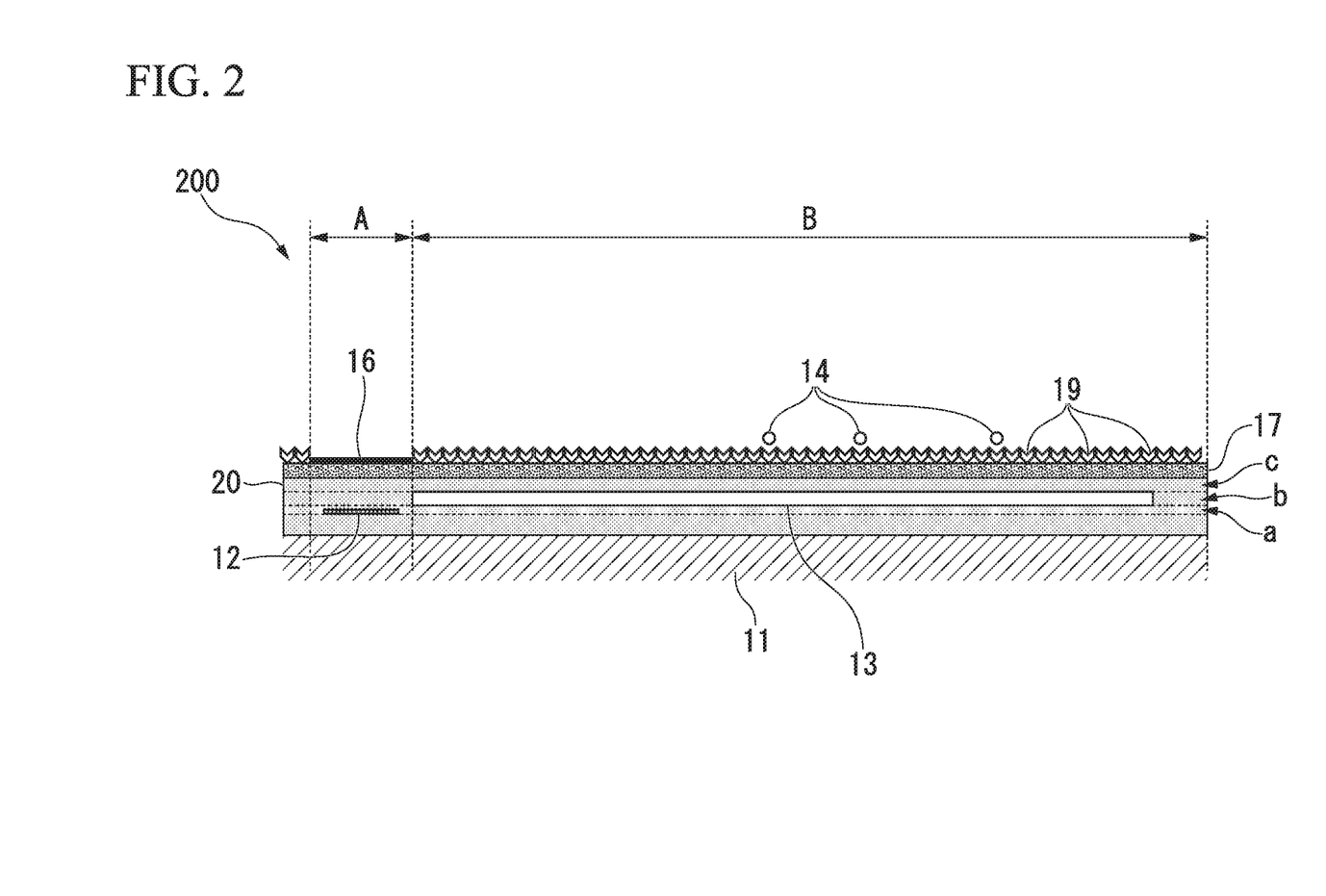
FIG. 2 is a cross-sectional view schematically showing a biosensor according to a second embodiment of the present disclosure.

FIG. 2 is a cross-sectional view schematically showing a biosensor according to a second embodiment of the present disclosure. Here, in the drawings following FIG. 2, components that are the same as those shown in the drawings explained above are denoted with the same reference numerals as in the drawings explained above, and details thereof will not be described.

A biosensor 200 is the same as the biosensor 100 shown in FIG. 1 except that a protective film is composed of a plurality of films. That is, in the biosensor 200, a second protective film 20 is laminated on one surface of the substrate 11. In addition, the magnetoresistance effect element 12 is disposed on the first plane a in the second protective film 20, and the soft magnetic thin film 13 is disposed on the second plane b in the second protective film 20. In addition, the second protective film 20 is laminated on a third plane c which is a surface of the soft magnetic thin film 13. In addition, the protective film 17 is laminated on both the first region A and the second region B on the surface of the second protective film 20. In addition, the MR cover film 16 is laminated on the surface of the protective film 17 on the first region A. In addition, the surface of the protective film 17 on the second region B contains the affinity substance 19. In other words, the second protective film 20 and the protective film 17 are laminated on both the first region A and the second region B on the soft magnetic thin film 13 in that order.

In the biosensor 200, the MR cover film is substantially free of the affinity substance 19, and the MR cover film 16, the protective film 17 and the second protective film 20 are made of different materials.

The biosensor 200 shown in FIG. 2 is used to detect biomolecules in a sample based on the same principle as in the biosensor 100 shown in FIG. 1.

Third Embodiment

Figure 3:
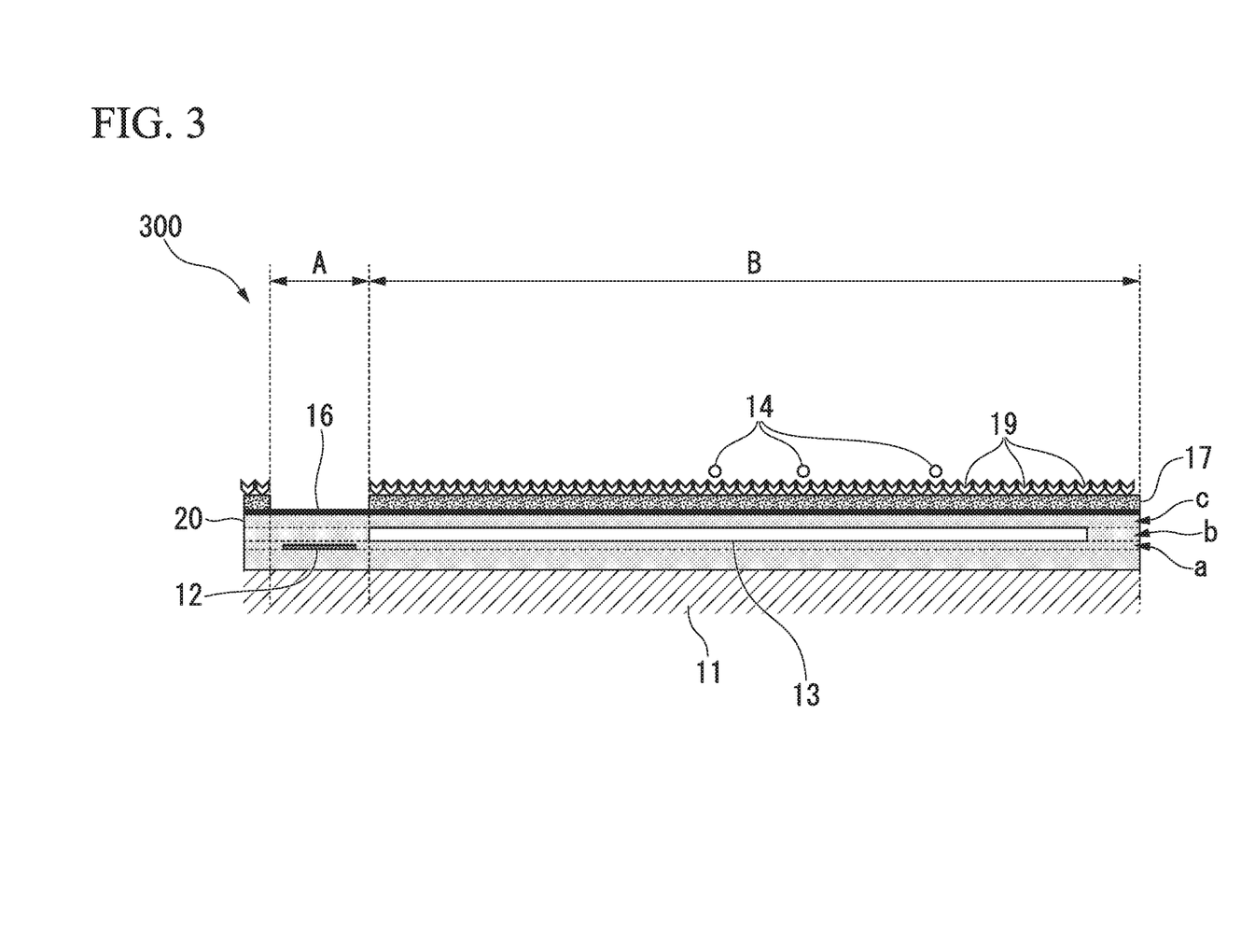
FIG. 3 is a cross-sectional view schematically showing a biosensor according to a third embodiment of the present disclosure.

FIG. 3 is a cross-sectional view schematically showing a biosensor according to a third embodiment of the present disclosure.

A biosensor 300 is the same as the biosensor 200 shown in FIG. 2 except that an MR cover layer is disposed on both the first region A and the second region B. That is, in the biosensor 300, the second protective film 20 is laminated on one surface of the substrate 11. In addition, the magnetoresistance effect element 12 is disposed on the first plane a in the second protective film 20. In addition, the soft magnetic thin film 13 is disposed on the second plane b in the second protective film 20. In addition, the second protective film 20 is laminated on the third plane c which is a surface of the soft magnetic thin film 13. In addition, the MR cover film 16 is laminated on both the first region A and the second region B on the surface of the second protective film 20. In addition, the protective film 17 is laminated on the surface of the MR cover film 16 on the second region B. In addition, the surface of the protective film 17 on the second region B contains the affinity substance 19. In other words, in the second region B, the MR cover film 16 that is interposed between the second protective film 20 and the protective film 17 is disposed.

In the biosensor 300, the MR cover film is substantially free of the affinity substance 19, and the MR cover film 16, the protective film 17 and the second protective film 20 are made of different materials.

The biosensor 300 shown in FIG. 3 is used to detect biomolecules in a sample based on the same principle as in the biosensor 100 shown in FIG. 1.

Fourth Embodiment

Figure 4:
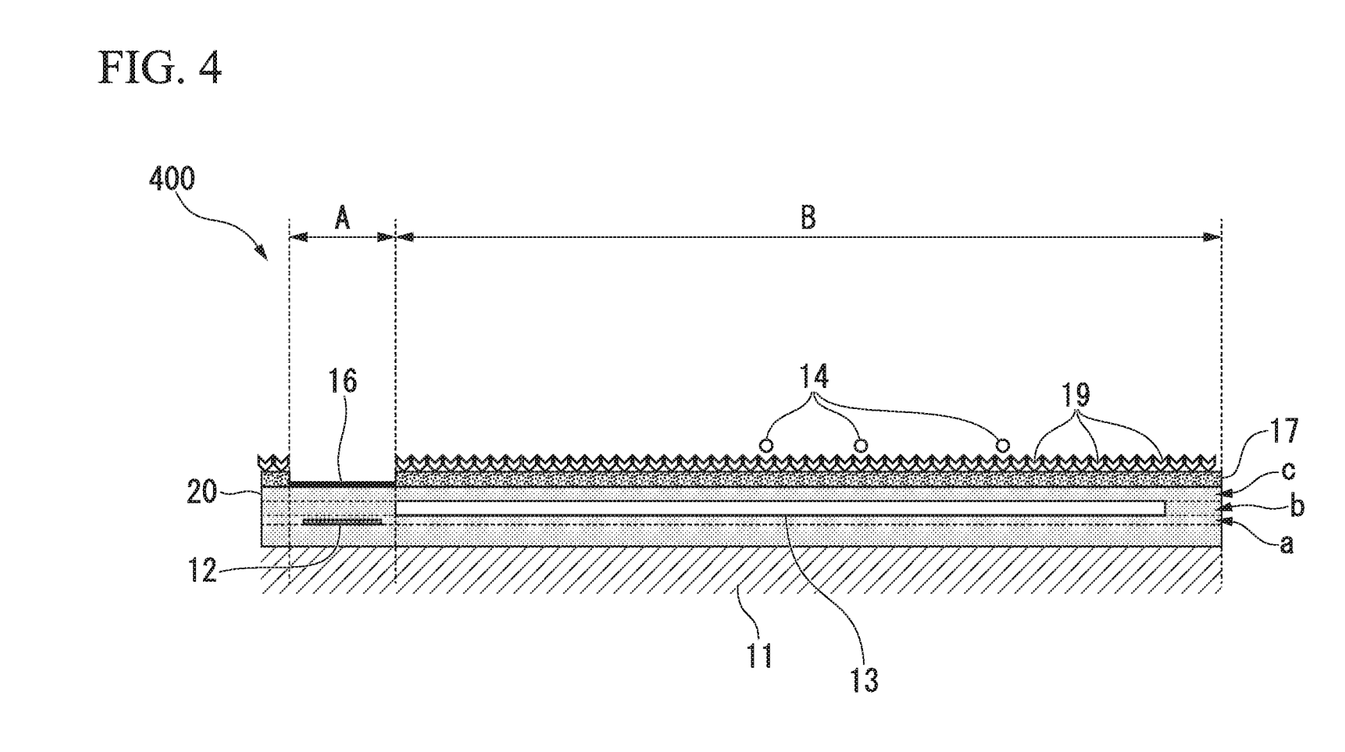
FIG. 4 is a cross-sectional view schematically showing a biosensor according to a fourth embodiment of the present disclosure.

FIG. 4 is a cross-sectional view schematically showing a biosensor according to a fourth embodiment of the present disclosure.

A biosensor 400 is the same as the biosensor 200 shown in FIG. 2 except that the MR cover film 16 is disposed on the top part of the first region A, and the protective film 17 is disposed on the top part of the second region B. That is, in the biosensor 400, the second protective film 20 is laminated on one surface of the substrate 11. In addition, the magnetoresistance effect element 12 is disposed on the first plane a in the second protective film 20. In addition, the soft magnetic thin film 13 is disposed on the second plane b in the second protective film 20. In addition, the second protective film 20 is laminated on the third plane c which is a surface of the soft magnetic thin film 13. In addition, the MR cover film 16 is laminated on the surface of the second protective film 20 on the first region A. In addition, the protective film 17 is laminated on the surface of the second protective film 20 on the second region B. In addition, the surface of the protective film 17 on the second region B contains the affinity substance 19. In other words, the MR cover film 16 is disposed on the top part of the first region A, and the protective film 17 is disposed on the top part of the second region.

In the biosensor 400, the MR cover film 16 is substantially free of the affinity substance 19, and the MR cover film 16, the protective film 17 and the second protective film 20 are made of different materials.

The biosensor 400 shown in FIG. 4 is used to detect biomolecules in a sample based on the same principle as in the biosensor 100 shown in FIG. 1.

The biosensor according to the present embodiment is not limited to those shown in FIGS. 1 to 4, and a biosensor in which some components of those shown in FIGS. 1 to 4 are modified or deleted and a biosensor in which other components are additionally added to those described above may be used as long as effects thereof are not impaired.

© Components of Biosensor

Components of a biosensor according to the present embodiment will be described below in detail.

○ Substrate

As a material of the substrate, for example, a semiconductor such as silicon and AlTiC or a conductor, or a material made of an insulator such as alumina or glass may be exemplified, and a form thereof is not particularly limited.

The thickness of the substrate is not particularly limited, but it may be, for example, 400 μm or more and 2000 μm or less. When the thickness of the substrate is in such a range, it is possible to obtain a thin and lightweight biosensor having an appropriate strength.

Here, "the thickness of the substrate" refers to the thickness of the entire substrate. For example, the thickness of the substrate composed of a plurality of layers refers to the total thickness of all layers constituting the substrate.

○ Magnetoresistance Effect Element

The magnetoresistance effect element is not particularly limited as long as it is an element that uses a phenomenon in which a magnetic field influence is received and an electrical resistance changes. The magnetoresistance effect element is preferably an element of a type including a magnetization fixed layer having a magnetization direction fixed in a certain direction in the plane of the laminate and a magnetization free layer whose magnetization direction changes according to an external magnetic field. In addition, in the magnetoresistance effect element, preferably, a magnetization fixed direction of the magnetization fixed layer is substantially parallel or substantially antiparallel to a direction of a leakage magnetic field which is a magnetic field input from an end surface of the soft magnetic thin film and is a film surface direction of the magnetoresistance effect element.

In the present embodiment, description including the terms substantially parallel or substantially antiparallel means approximately parallel or anti-parallel, and includes deviation within a range of 0.1° or more and 10° or less.

In addition, the magnetoresistance effect element includes a magnetization fixed layer, an intermediate layer made of a nonmagnetic conductor or an insulator, and a magnetization free layer, and preferably includes a laminate including the intermediate layer interposed between the magnetization fixed layer and the magnetization free layer.

Here, when the intermediate layer is made of a nonmagnetic conductor, the magnetoresistance effect element is generally called a giant magnetoresistive (GMR) effect element and when the intermediate layer is made of an insulator, the magnetoresistance effect element is called a tunnel type magnetoresistive (TMR) effect element. A resistance of the magnetoresistance effect element changes according to an angle between a magnetization direction of the magnetization fixed layer and an average magnetization direction of the magnetization free layer. Generally, the magnetization direction of the magnetization fixed layer is defined as a magnetic sensing direction.

The magnetization free layer is made of, for example, a soft magnetic film of NiFe or the like. The intermediate layer is made of, for example, a conductor film of Cu or the like or an insulator film of an alumina-magnesium oxide or the like.

The magnetization fixed layer is made of an antiferromagnetic film and a magnetization fixed film, and the magnetization fixed film is in contact with the intermediate layer. The antiferromagnetic film is made of, for example, an antiferromagnetic Mn alloy such as IrMn and PtMn. The magnetization fixed film is made of, for example, a ferromagnetic material such as CoFe and NiFe, or may have a configuration in which a Ru thin film layer is interposed between CoFe layers or the like.

○ Soft Magnetic Thin Film

The soft magnetic thin film has the following two functions.

(1) Function of changing a direction of a magnetic field (applied magnetic field) applied in substantially a normal direction of a lamination surface, and generating a magnetic field component in a magnetic sensing direction of a magnetoresistance effect element as a leakage magnetic field (detection magnetic field) at the end of a lamination surface of the soft magnetic thin film, and (2) Function of transmitting a component in the in-plane direction of the laminate of a stray magnetic field of magnetic beads accumulated on the soft magnetic thin film to the magnetoresistance effect element Preferably, the soft magnetic thin film is disposed on the same straight line in a magnetization fixed direction of the magnetoresistance effect element 2 when viewed in an application direction of a magnetic field applied to the soft magnetic thin film. A projection plane of the soft magnetic thin film in a normal direction of the main surface of the substrate is close to a projection plane of the magnetoresistance effect element in a normal direction of the main surface of the substrate. In addition, they may partially overlap. Preferably, the soft magnetic thin film is made of, for example, a permalloy.

The size of the soft magnetic thin film is appropriately selected according to the number and size of magnetic beads to be captured. However, the size is preferably 0.1 μm or more and 1000 μm or less square, more preferably 0.5 μm or more and 500 μm or less square, and particularly preferably 50 μm or more and 200 μm or less square.

The thickness of the soft magnetic thin film is preferably 0.01 μm or more and 100 μm or less, more preferably 0.1 μm or more and 50 μm or less, and particularly preferably 0.5 μm or more and 5 μm or less.

○ Magnetic Beads

The magnetic beads are not particularly limited as long as they are magnetic particles. For example, iron oxide particles may be exemplified. The diameter of the magnetic beads depends on the balance with the area of the protective film. For example, the diameter is preferably 0.01 μm or more and 100 μm or less, more preferably 0.05 μm or more and 50 μm or less, and particularly preferably 0.1 μm or more and 5 μm or less.

The magnetic beads contain a second affinity substance that specifically binds to biomolecules, and capture biomolecules via the second affinity substance. The magnetic beads may be magnetic beads to which a second affinity substance is added by a coating treatment or the like or magnetic beads composed of the second affinity substance itself.

Preferably, the surface of the magnetic beads is coated with a polymer or silica matrix according to biomolecules to be captured. When ligands are desired to be captured as biomolecules, the surface of the magnetic beads is preferably hydrophilic, and when antibodies are desired to be captured as biomolecules, the surface of the magnetic beads is preferably hydrophobic.

○ Protective Film

The protective film is not particularly limited as long as it can protect the soft magnetic thin film. Examples of the material of the protective film include oxides such as alumina, silica, titanium oxide, zirconium oxide, indium oxide, tartaric oxide, zinc oxide, gallium oxide, and tin oxide; noble metals such as gold, silver, platinum, rhodium, ruthenium, and palladium; and inorganic substances such as aluminum nitride, and silicon nitride, and organic substances such as a polyimide.

The protective film may be composed of one layer (single layer) or a plurality of layers such as two or more layers. In addition, when the protective film is composed of a plurality of layers, the plurality of layers may be the same as or different from each other, and combinations of the plurality of layers are not particularly limited.

The thickness of the protective film is preferably 1 nm or more and 1000 nm or less, more preferably 1 nm or more and 100 nm or less, and particularly preferably 1 nm or more and 15 nm or less.

Here, "the thickness of the protective film" refers to the thickness of the entire protective film. For example, the thickness of the protective film composed of a plurality of layers refers to the total thickness of all layers constituting the protective film.

The outer surface of the protective film is a surface that comes in contact with biomolecules in a sample. The outer surface contains a first affinity substance that specifically binds to biomolecules to be detected. In addition, the magnetic beads also contain a second affinity substance that specifically binds to biomolecules.

When these affinity substances are contained, biomolecules are fixed to the outer surface of the protective film via the first affinity substance only if there are biomolecules to be detected in a sample (in a specimen). Next, magnetic beads bind to biomolecules via the second affinity substance and thus the magnetic beads are fixed to the surface of the protective film.

Examples of the biomolecules to be detected include nucleic acids (that may be naturally derived or chemically synthesized) such as DNA, mRNA, miRNA, siRNA, and artificial nucleic acids (for example, locked nucleic acid (LNA), bridged nucleic acid (BNA)); peptides such as ligands, cytokines, and hormones; proteins such as receptors, enzymes, antigens, and antibodies; cells, viruses, bacteria, and fungi.

Examples of the sample containing biomolecules to be detected include blood, serum, plasma, urine, buffy coat, saliva, semen, thoracic exudates, cerebrospinal fluids, tears, sputum, mucosa, lymph fluids, abdominal fluids, pleural effusion, amniotic fluids, bladder irrigation fluids, bronchoalveolar lavage fluids, cell extraction liquids, and cell culture supernatants.

In addition, the biomolecules to be detected may be biomolecules to be detected with which other biomolecules are complexed or biomolecules to be detected which are converted into other biomolecules. For example, a complex obtained by hybridizing DNA having biotin at the end with RNA (hereinafter referred to as an "RNA-DNA-biotin complex") may be exemplified. When biotin is added to RNA by complexation, it can be specifically bound to streptavidin. Therefore, for example, when RNA or DNA that is hybridizable with a nucleic acid part in which RNA or DNA contained in the RNA-DNA-biotin complex is not hybridized is used as the first affinity substance, they are captured on the biosensor of the present embodiment. In addition, when streptavidin is used as the second affinity substance, it is possible to specifically detect the RNA-DNA-biotin complex.

For the first affinity substance and the second affinity substance which specifically bind to biomolecules, when biomolecules to be detected are nucleic acids, nucleic acids complementary to the nucleic acids may be exemplified. When biomolecules to be detected are antigens, antibodies having affinity for antigens may be exemplified. When biomolecules to be detected are primary antibodies, antigens having affinity for primary antibodies and secondary antibodies may be exemplified. When biomolecules to be detected are cells, viruses, bacteria, fungi, or the like, antibodies that recognize antigens presented on surfaces thereof may be exemplified.

When biomolecules to be detected are miRNA present in blood, for example, a first nucleic acid complementary to 10 bases at the 5' end of miRNA may be exemplified as the first affinity substance and a second nucleic acid complementary to 10 bases at the 3' end of miRNA may be exemplified as the second affinity substance.

When biomolecules to be detected are antigen proteins present in blood, for example, first antibodies that recognize the antigen proteins may be exemplified as the first affinity substance, and second antibodies that recognize the antigen proteins and have a different epitope from the first antibodies may be exemplified as the second affinity substance.

When the first affinity substance is an antibody, the antibody can be prepared, for example, by immunizing a rodent animal such as a mouse with a labeled peptide as an antigen. In addition, for example, this can be prepared by phage library screening. The antibody may be an antibody fragment and Fv, Fab, scFv, and the like may be exemplified as the antibody fragment.

While an example in which magnetic beads are bound to biomolecules fixed to the surface of the protective film has been exemplified in the above description, the present embodiment is not limited thereto. Biomolecules to be detected may be bound to magnetic beads in advance, and they may be brought into contact with the surface of the protective film as a sample.

As a method of fixing magnetic beads to the surface of the protective film covering the soft magnetic thin film, any technology that has been developed in the past or will be developed in the future can be applied and any method may be used as long as it is possible to indirectly detect the presence of biomolecules to be detected by measuring magnetic beads.

《Method of Fixing Affinity Substance to Protective Film》

As a method of fixing an affinity substance to a surface of a protective film, for example, when a constituent material of the protective film disposed on the top part is a noble metal, a thiol group, an isothiocyanate group or a disulfide group derived from the affinity substance or introduced into the affinity substance forms a thiolate bond with the surface of the noble metal, and the affinity substance can be fixed.

In addition, when a constituent material of the protective film disposed on the top part is an oxide, it is possible to fix the affinity substance via a silane coupling agent or phosphonic acid derivatives having a functional group that can bind to the affinity substance.

The functional group is not particularly limited as long as it is a group that can be covalently bonded or non-covalently bonded to the affinity substance. For example, a chemically active (that is, activated so that the reactivity with the first affinity substance becomes higher) group, a receptor group, and a ligand group may be exemplified. The affinity substance may be modified so that a covalent bond or non-covalent bond with a functional group can be made.

As a specific example, an activated carboxyl-derived group, carboxyl group, an aldehyde group, an epoxy group, a vinyl sulfone group, a biotinyl group, a thiol group, an amino group, an isocyanate group, an isothiocyanate group, a hydroxyl group, an acrylate group, a maleimide group, a hydrazide group, an aminooxy group, an azide group, an amide group, a sulfonate group, avidin, streptavidin, and a metal chelate may be exemplified, but the present disclosure is not limited thereto. Among these, generally, since many of the affinity substances have an amino group, in consideration of the reactivity with the amino group, an aldehyde group, an activated carboxyl-derived group, an epoxy group, and a vinylsulfone group are preferable and a biotinyl group having a high coupling constant is preferable. In particular, when the first affinity substance has an amino group and is bonded via the amino group, an activated carboxyl-derived group is preferable in consideration of the balance between the reactivity with the amino group and the storage stability. On the other hand, when first affinity substance has an aldehyde group and is bonded via the aldehyde group, since the reactivity is high, an aminooxy group or a hydrazide group is preferable.

As the phosphonic acid derivatives, for example, alkylphosphonic acid, alkenylphosphonic acid, and phenylphosphonic acid may be exemplified. As the phosphonic acid derivatives, more specifically, vinylphosphonic acid ($CH_2$=CH—$PO_3H_2$), propene-1-phosphonic acid ($CH_3$—CH=CH—$PO_3H_2$), and propene-2-phosphonic acid ($CH_2$=CH($CH_3$)—$PO_3H_2$) may be exemplified and those into which a functional group is introduced may be used. As phosphonic acid derivatives having a functional group, for example, 2,5-dicarboxyphenylphosphonic acid, 3,5-dicarboxyphenylphosphonic acid, and 2,5-bisphosphonoterephthalic acid may be exemplified.

As a silane coupling agent having a functional group, for example, trimethoxysilylbenzoic acid, γ-methacryloxypropyltrimethoxysilane, vinyltriacetoxysilane, vinyltrimethoxysilane, γ-isocyanatopropyltriethoxysilane, γ-glycidoxypropyltrimethoxysilane, β-(3,4-epoxycyclohexyl)ethyltrimethoxysilane, tris-(3-trimethoxysilylpropyl)isocyanurate, methacryloxypropyldimethylmethoxysilane, methacryloxypropyldimethylethoxysilane, methacryloxypropylmethyldimethoxysilane, methacryloxypropylmethyldiethoxysilane, methacryloxypropyltrimethoxysilane, methacryloxypropyltriethoxysilane, 3-mercaptopropyltrimethoxysilane, 3-mercaptopropyltriethoxysilane, 3-mercaptopropylmethyldimethoxysilane, 3-mercaptopropylmethyldiethoxysilane, 3-mercaptopropyldimethylmethoxysilane, 3-mercaptopropyldimethylethoxysilane, and mercaptoethyltriethoxysilane may be exemplified.

A more specific method of fixing the affinity substance to the surface of the protective film can be determined by those skilled in the art by a known method according to a type of the affinity substance. For example, a method in which a solution containing an affinity substance is brought into contact with a protective film together with a silane coupling agent or phosphonic acid derivatives having a functional group that covalently bonds with the affinity substance may be exemplified.

For example, when a material constituting the protective film is an oxide and an affinity substance having an amino group is fixed via a silane coupling agent having a carboxyl group, if the surface of the protective film that is in contact with a solution in which a first affinity substance and a silane coupling agent are mixed into a general buffer solution with a pH of 7.0 or more and 10.0 or less is incubated for a predetermined time, the amino group of the affinity substance and the carboxyl group of the silane coupling agent react to form an amide bond, and additionally the silane coupling agent and the surface of the protective film react to form an ether bond, and thus the affinity substance can be fixed to the outer surface of the protective film. Examples of the buffer solution include a phosphate buffer solution, and a tris buffer solution.

○ MR Cover Film

The MR cover film is not particularly limited as long as it can protect the magnetoresistance effect element. Examples of the material of the MR cover film include oxides such as alumina, silica, titanium oxide, zirconium oxide, indium oxide, tartaric oxide, zinc oxide, gallium oxide, and tin oxide; and inorganic substances of noble metals such as gold, silver, platinum, rhodium, ruthenium, and palladium.

In addition, when a material constituting the protective film is a noble metal, a material constituting the MR cover film is preferably an oxide. On the other hand, when a material constituting the protective film is an oxide, a material constituting the MR cover film is preferably a noble metal.

When materials constituting the protective film and the MR cover film are different from each other and additionally combined as above, the affinity substance is selectively fixed only to the protective film. In addition, the MR cover layer is substantially free of the affinity substance, and nonspecific adsorption of biomolecules or magnetic beads to the MR cover film is reduced. Thus, variation in GMR outputs is reduced, and it is possible to detect biomolecules in a sample with high accuracy and high sensitivity.

The MR cover film may be composed of one layer (single layer) or a plurality of layers such as two or more layers. When the MR cover layer is composed of a plurality of layers, the plurality of layers may be the same as or different from each other, and combinations of the plurality of layers are not particularly limited.

The thickness of the MR cover film is preferably 1 nm or more and 1000 nm or less, more preferably 1 nm or more and 100 nm or less, and particularly preferably 1 nm or more and 15 nm or less.

Here, "the thickness of the MR cover film" refers to the thickness of the entire MR cover film. For example, the thickness of the MR cover film composed of a plurality of layers refers to the total thickness of all layers constituting the MR cover film.

In addition, the MR cover film preferably contains a substance (nonspecific adsorption inhibiting substance) that reduces nonspecific adsorption of biomolecules to the outer surface. When the MR cover film contains the nonspecific adsorption inhibiting substance, it is possible to more effectively reduce nonspecific adsorption of biomolecules or magnetic beads.

The nonspecific adsorption inhibiting substance may be any monomer or polymer as long as it has a fixing group on the MR cover film at an end and has a biocompatible group at the other end or in a compound.

When a material constituting the MR cover film is a noble metal, examples of the fixing group include a thiol group, an isothiocyanate group, and a disulfide group. On the other hand, when a material constituting the MR cover film is an oxide, examples of the fixing group include an alkoxysilane group and a phosphonic acid group.

The biocompatible group has an excellent nonspecific adsorption inhibiting effect. As the biocompatible group, specifically, a phosphorylcholine group, (poly)alkylene glycol residues, a sulfoalkyl amino group, and the like may be exemplified. As the nonspecific adsorption inhibiting substance in the present embodiment, for example, a polymer compound having a biocompatible group that is produced by polymerizing monomers having such a biocompatible group may be produced and used.

When the nonspecific adsorption inhibiting substance is a monomer, the nonspecific adsorption inhibiting substance is subjected to molecular self assembly (MSA) and forms a monomolecular film.

In this specification, "molecular self assembly" means that tissues or structures are naturally formed by molecules themselves without being controlled by external factors.

In the nonspecific adsorption inhibiting substance in the present embodiment, a weak intermolecular bond such as Van der Waals coupling is used, nonspecific adsorption inhibiting substances are aligned and bonded to form one monomolecular film (self-assembled monolayers (SAMs)).

Examples of the monomer having a phosphorylcholine group include (meth)acryloyloxyalkylphosphorylcholines such as 2-methacryloyloxyethyl phosphorylcholine and 6-methacryloyloxyhexylphosphorylcholine; (meth)acryloyloxyalkoxyalkylphosphorylcholines such as 2-methacryloyloxyethoxyethyl phosphorylcholine and 10-methacryloyloxyethoxy nonyl phosphorylcholine; and alkenyl phosphorylcholines such as allyl phosphorylcholine, butenylphosphorylcholine, hexenyl phosphorylcholine, octenyl phosphorylcholine, and decenyl phosphorylcholine. As the nonspecific adsorption inhibiting substance of the present embodiment, those in which the fixing group is introduced into an end opposite to the phosphocholine group may be used.

In this specification, "alkylene glycol residue" refers to an alkyleneoxy group (—R—O—, here, R denotes an alkylene group) which remains after hydroxyl groups at one end or both ends of an alkylene glycol (HO—R—OH, here, R denotes an alkylene group) undergo a condensation reaction with another compound. For example, in the case of methylene glycol (HO—$CH_2$—OH), the alkylene glycol residue is a methyleneoxy group (—$CH_2$—O—), and in the case of ethylene glycol (HO—$CH_2CH_2$—OH), the alkylene glycol residue is an ethyleneoxy group (—$CH_2CH_2$—O—). In addition, "polyalkylene glycol residue" refers to a structure in which a plurality of alkyleneoxy groups are repeated.

Examples of the monomer having an alkylene glycol residue include methoxy polyethylene glycol (meth)acrylate, ethoxypolyethylene glycol (meth)acrylate, 2-hydroxyethyl (meth)acrylate and monosubstituted esters of its hydroxyl group, 2-hydroxypropyl (meth)acrylate and monosubstituted esters of its hydroxyl group, 2-hydroxybutyl (meth)acrylate and monosubstituted esters of its hydroxyl group, glycerol mono (meth)acrylate, (meth)acrylate having polypropylene glycol as side chain, 2-methoxyethyl (meth)acrylate, 2-ethoxyethyl (meth)acrylate, methoxydiethylene glycol (meth)acrylate, ethoxydiethyleneglycol (meth)acrylate, and ethoxypolyethylene glycol (meth)acrylate. In addition, the average number of repetitions of the alkylene glycol residue is preferably 5 or more and 90 or less.

When the average number of repetitions of the alkylene glycol residue is within the above range, excellent operability (handling) during synthesis is obtained.

As the nonspecific adsorption inhibiting substance of the present embodiment, those in which the fixing group is introduced into any end of the monomer having the alkylene glycol residue may be used.

Examples of the monomer having a sulfoalkyl amino group include N-methyl-N-(3-sulfopropyl)acrylamide, 3-(N,N-dimethylmyristylammonio)propanesulfonic acid (3-(N,N-dimethylmyristylammonio)propanesulfonate, and SB3-14, myristyl sulfobetaine). As the nonspecific adsorption inhibiting substance of the present embodiment, those in which the fixing group is introduced into an end opposite to such a sulfo group may be used.

As a method of introducing the fixing group into a monomer having the biocompatible group, a known method may be used according to a fixing type to be introduced. For example, when the fixing group is a thiol group, within the monomer having the biocompatible group, at least one hydrogen bonded to carbon into which a fixing group is introduced is substituted with a halogen atom (for example, chlorine, bromine, iodine, etc.), and hydrogen sulfide is then reacted in the presence of alkali, and thus a thiol group can be introduced.

Alternatively, the biocompatible group may be introduced into the silane coupling agent or phosphocholine derivatives exemplified in the above «Method of fixing affinity substance to protective film» using a known method.

As the nonspecific adsorption inhibiting substance of the present embodiment, more specifically, for example, 3-[(11-mercaptoundecyl)-N,N-dimethylammonio] propanesulfonate which is a sulfobetaine type alkane thiol may be exemplified.

«Method of Fixing Nonspecific Adsorption Inhibiting Substance to MR Cover Film»

As a method of fixing the nonspecific adsorption inhibiting substance to the surface of the MR cover film, for example, when a constituent material of the MR cover film is a noble metal, a nonspecific adsorption inhibiting substance having a thiol group, an isothiocyanate group or a disulfide group as a fixing group may be used, and the fixing group and the surface of the noble metal form a thiolate bond, and the nonspecific adsorption inhibiting substance can be fixed.

In addition, when a constituent material of the MR cover film is an oxide, a nonspecific adsorption inhibiting substance having an alkoxysilane group or a phosphonic acid group as a fixing group may be used and the fixing group and the surface of the oxide form an ether bond, and the nonspecific adsorption inhibiting substance can be fixed.

A more specific method of fixing the nonspecific adsorption inhibiting substance to the surface of the MR cover film can be determined by those skilled in the art by a known method according to a constituent material of the MR cover film. For example, a method in which a solution containing a nonspecific adsorption inhibiting substance is brought into contact with an MR cover film may be exemplified.

For example, when a material constituting the protective film is an oxide and a nonspecific adsorption inhibiting substance having an alkoxysilane group is fixed, if the surface of the MR cover film that is in contact with a solution in which a nonspecific adsorption inhibiting substance is mixed into a general buffer solution with a pH of 7.0 or more and 10.0 or less is incubated for a predetermined time, the nonspecific adsorption inhibiting substance can be fixed to the surface of the MR cover layer via an ether bond. Examples of the buffer solution include a phosphate buffer solution, and a tris buffer solution.

○ Other Components

• Electrode Terminal

The electrode terminal is disposed on a fourth plane which is a plane different from the magnetoresistance effect element and the soft magnetic thin film. In addition, the electrode terminal is connected to the magnetoresistance effect element via an internal wiring and can output a change in resistance of the magnetoresistance effect element as an output to the outside. For example, conductive metals such as Au, Al, Ag, and Cu or alloys thereof are preferably used for the electrode terminal and the internal wiring.

• Insulating Layer

The magnetoresistance effect element, the soft magnetic thin film, and the electrode terminal are separated by an insulating layer and an electrical short circuit between components can be prevented. In addition, when the substrate is made of a conductive material, the insulating layer is formed on the main surface of the substrate, and an electrical short circuit via the substrate can be prevented. For example, an inorganic substance such as alumina, aluminum nitride, silicon oxide, and silicon nitride or an organic substance such as a polyimide is preferably used for the insulating layer.

• Applied Magnetic Field and Detection Magnetic Field

When magnetic beads accumulate on the protective film via biomolecules and a magnetic field (applied magnetic field) is applied in a direction crossing the soft magnetic thin film, a detection magnetic field (leakage magnetic field) is input to the magnetoresistance effect element. A direction of the applied magnetic field is preferably perpendicular to the main surface of the magnetoresistance effect element. The applied magnetic field is not particularly limited, and is preferably 0.1 m tesla or more and 100 m tesla or less and more preferably 1 m tesla or more and 10 m tesla or less.

In the case of the applied magnetic field, the leakage magnetic field is preferably 1 n tesla or more and 10 m tesla or less, more preferably 10µ tesla or more and 5 m tesla or less, and particularly preferably 50µ tesla or more and 1 m tesla or less.

The detection magnetic field (leakage magnetic field) is influenced by a proportion of magnetic beads occupying the main surface of the magnetoresistance effect element via the protective film. As the number of magnetic beads accumulated on the protective film increases, a detected resistance value increases. The number of magnetic beads accumulated on the protective film and the detected resistance value via the leakage magnetic field are linearly correlated.

Then, based on the titer (for example, the number of biomolecules that the second affinity substance captures) of the second affinity substance included in the magnetic beads, it is possible to calculate the number of biomolecules accumulated on the protective film.

That is, according to the biosensor of the present embodiment, the number of biomolecules contained in a sample can be calculated. In this manner, in the biosensor of the present embodiment, it is possible to secure quantitation of biomolecules in a sample with high accuracy.

In addition, the biosensor of the present embodiment has high sensitivity, and can perform detection at a level of tens of nanotesla. Specifically, it is possible to detect an increase or decrease of 10 with respect to 1500 magnetic beads. That is, a change of about 0.5% can be detected.

In addition, since the biosensor of the present embodiment uses magnetic beads, it has higher sensitivity and a longer lifespan compared to fluorescence. Therefore, it is much better than a detection method such as ELISA.

◇ Method of Producing Biosensor

The biosensor of the present embodiment can be produced using a known method according to sequential lamination so that it has a corresponding positional relationship among the above components.

In addition, a method of fixing an affinity substance to a protective film is the same as the «Method of fixing affinity substance to protective film» described above.

In addition, a method of fixing a nonspecific adsorption inhibiting substance to an MR cover film is the same as the «Method of fixing nonspecific adsorption inhibiting substance to MR cover film» described above.

◇ Method of Using Biosensor

© Method of Detecting a Biomolecule

The biosensor of the present embodiment can be used for, for example, a method of detecting a biomolecule to be described below.

First, a sample containing biomolecules is brought into contact with a protective film, and the biomolecules accumulate on the protective film via the first affinity substance (Process 1). Next, magnetic beads are brought into contact with the protective film and accumulate on the protective film via the biomolecules (Process 2). Next, a magnetic field is applied in a direction crossing a soft magnetic thin film, a detection magnetic field is input to the magnetoresistance effect element, and a resistance value is detected (Process 3).

The processes will be described in detail.

[Process 1]

Process 1 is a process in which a sample containing biomolecules is brought into contact with a protective film and the biomolecules accumulate on the protective film via a first affinity substance. In consideration of convenience and the like, the biosensor is preferably used in a microfluidic device. In Process 1, first, a sample containing biomolecules flow through a micro flow path. The sample not particularly limited as long as it contains biomolecules to be detected. As a sample, for example, when the method of detecting a biomolecule of the present embodiment is used for diagnosis of a disease, a sample derived from a subject such as a person in whom onset of a disease was confirmed or a person in whom onset of a disease was suspected, or a sample derived from a subject such as a patient being treated for a disease may be exemplified. As the sample, more specifically, the same as those exemplified in "○ Protective film" above may be used.

For example, when peptides and proteins such as antigens and receptors present on the surface of blood circulating tumor cells are to be detected, a sample may be caused to directly flow through the micro flow path. For example, it has been reported that miRNA is involved in onset and progress of cancer, cardiovascular diseases, neurodegenerative diseases, mental illness, chronic inflammatory diseases and the like. When nucleic acids such as genomic DNA, cDNA, Total RNA, mRNA, and rRNA including miRNA are to be detected, a nucleic acid is preferably extracted from the biological sample. The extraction method is appropriately selected from conventional methods according to a type of nucleic acid.

Biomolecules in a sample which flows through a micro flow path are captured by the first affinity substance on the protective film and accumulate on the protective film. As the first affinity substance, nucleic acids, antibodies, and the like may be exemplified as described above. The biomolecules form a complex with the first affinity substance on the protective film according to hybridization, an antigen and antibody reaction, and the like.

After the first affinity substance-biomolecule complex is formed on the protective film, the protective film is preferably washed using a buffer solution or the like. According to washing, impurities that are nonspecifically bound to the protective film can be removed and detection accuracy of the biomolecules can be improved. Examples of the buffer solution include a phosphate buffer solution, and a tris buffer solution.

[Process 2]

Process 2 is a process in which magnetic beads are brought into contact with a protective film and accumulate on the protective film via the biomolecules. As described above, the magnetic beads contain a second affinity substance that captures biomolecules. For example, when magnetic beads flow through a micro flow path and come in contact with the protective film, they bind to biomolecules in the first affinity substance-biomolecule complex formed on the protective film via the second affinity substance. In Process 2, a first affinity substance-biomolecule-second affinity substance complex is formed on the protective film. That is, the magnetic beads containing the second affinity substance accumulate on the protective film.

After the first affinity substance-biomolecule-second affinity substance complex is formed on the protective film, the protective film is preferably washed with a buffer solution or the like as in Process 1. According to washing, the magnetic beads that are nonspecifically bound to the protective film can be removed, and detection accuracy of the biomolecules can be improved. As the buffer solution, the same ones exemplified in [Process 1] may be exemplified.

[Process 3]

Process 3 is a process in which a magnetic field is applied in a direction crossing the soft magnetic thin film, a detection magnetic field is input to the magnetoresistance effect element, and a resistance value is detected.

The detection magnetic field (leakage magnetic field) is influenced by a proportion of magnetic beads occupying the main surface of the magnetoresistance effect element via the protective film. As the number of magnetic beads accumulated on the protective film increases, a detected resistance value increases.

According to Process 3, it is possible to quantify accurately the number of magnetic beads accumulated on the protective film. Then, based on the titer (for example, the number of biomolecules that the second affinity substance captures) of the second affinity substance included in the magnetic beads, it is possible to calculate the number of all biomolecules accumulated on the protective film. That is, according to the detection method of the present embodiment, it is possible to calculate the number of biomolecules contained in a sample. Therefore, when there is a positive correlation between the number of biomolecules in a sample and a disease state, if the number of biomolecules in the sample is successively calculated, it is possible to perform follow-up observation of the disease state.

As described above, in the detection method of the present embodiment, it is possible to secure quantitation of biomolecules in a sample.

As another use example of the biosensor of the present embodiment, a method of detecting a biomolecule to be described below may be used.

First, a sample containing biomolecules and magnetic beads are mixed tighter and the biomolecules are captured by the magnetic beads via the second affinity substance (Process 4). Next, magnetic beads that have captured biomolecules are brought into contact with a protective film and the magnetic beads accumulate on the protective film via the biomolecules (Process 5). Next, a magnetic field is applied in a direction crossing the soft magnetic thin film, a detection magnetic field is input to the magnetoresistance effect element, and a resistance value is detected (Process 3).

Since this method is the same as the method of detecting a biomolecule including the above [Process 1] to [Process 3] except that, when a first affinity substance-biomolecule-second affinity substance complex is formed, a biomolecule-second affinity substance complex is formed in advance, description thereof will be omitted.

Ⓒ Biochip

The biosensor of the present embodiment can be applied to a biochip.

When a plurality of biosensors with different first affinity substances on the protective film are provided, the biochip of the present embodiment can comprehensively analyze properties of a sample.

As the biochip, for example, a biochip for cancer diagnosis, a biochip for carcinoma diagnosis, and a biochip for detecting influenza virus may be exemplified.

○ Biochip for Cancer Diagnosis

As the first affinity substance provided on the protective film, a nucleic acid complementary to a nucleic acid derived from a cancer gene or a cancer inhibiting gene may be exemplified. When there is a mutation specific to a cancer patient in the cancer gene or the cancer inhibiting gene, a nucleic acid complementary to the nucleic acid containing the mutation is preferable.

As the cancer gene, a gene group that encodes a growth factor such as sis; a gene group that encodes a receptor type tyrosine kinase such as erbB, fms, and ret; a gene group that encodes a non-receptor type tyrosine kinase such as fes; a gene group that encodes a GTP/GDP binding protein such as ras; a gene group that encodes a serine/threonine kinase such as src, mos, and raf; a gene group that encodes a nuclear protein such as myc, myb, fos, jun, and erbA; a gene group that encodes a signal transducing adapter molecule such as crk; and a fusion gene such as Bcr-Abl may be exemplified.

In addition, as the cancer gene, a Ras-MAP kinase pathway-linked gene such as Shc, Grb2, Sos, MEK, Rho, and Rac genes; a phospholipase C gamma-protein kinase C pathway-linked gene such as PLCγ and PKC; a PI3K-Akt pathway-linked gene such as PI3K, Akt, and Bad; a JAK-STAT pathway-linked gene such as JAK and STAT; and a GAP-related pathway-linked gene such as GAP, p180, and p62 may be exemplified.

Examples of the cancer inhibiting gene include RB, p53, WT1, NF1, APC, VHL, NF2, p16, p19, BRCA1, BRCA2, PTEN, and E cadherin gene.

In addition, as the first affinity substance, a substance that captures a protein which is a genetic product of the above genes, for example, an antibody (including an antibody fragment), an aptamer, a ligand, and a receptor may be used.

○ Biochip for Diagnosis for Specific Type of Cancer

In the biochip of the present embodiment, a first affinity substance provided on a protective film may be a nucleic acid complementary to a plurality of nucleic acids that are extracted from one type of cancer. That is, the biochip of the present embodiment may be a biochip for diagnosis of a specific type of cancer.

The target cancer is not particularly limited, and, for example, breast cancer (for example, invasive ductal carcinoma, noninvasive ductal carcinoma, Inflammatory breast cancer, etc.), prostate cancer (for example, hormone-dependent prostate cancer, hormone-independent prostate cancer, etc.), pancreatic cancer (for example, pancreatic duct cancer, etc.), stomach cancer (for example, papillary adenocarcinoma, mucinous adenocarcinoma, adenosquamous carcinoma, etc.), lung cancer (for example, non small cell lung cancer, small cell lung cancer, malignant mesothelioma, etc.), colon cancer (for example, familial colorectal cancer, hereditary nonpolyposis colorectal cancer, gastrointestinal stromal tumor, etc.), rectal cancer (for example, gastrointestinal stromal tumor, etc.), small intestine cancer (for example, non-Hodgkin's lymphoma, gastrointestinal stromal tumor, etc.), small intestine cancer (for example, non-Hodgkin's lymphoma, gastrointestinal stromal tumor, etc.), esophageal cancer, duodenal cancer, tongue cancer, pharyngeal cancer (for example, nasopharyngeal cancer, oropharyngeal cancer, hypopharyngeal cancer, etc.), head and neck cancer, salivary gland cancer, brain tumor (for example, pineal gland stellate cell tumor, pilocytic astrocytoma, diffuse astrocytoma, anapestic astrocytoma, etc.), schwannoma, liver cancer (for example, primary liver cancer, extrahepatic bile duct cancer, etc.), kidney cancer (for example, renal cell carcinoma, transitional epithelial carcinoma of the renal pelvis and ureter, etc.), gall bladder cancer, bile duct cancer, pancreatic cancer, liver cancer, endometrial cancer, cervical cancer, ovarian cancer (for example, epithelial ovarian cancer, extragonadal germ cell tumor, ovarian germ cell tumor, ovarian low grade tumor, etc.), bladder cancer, urethral cancer, skin cancer (for example, intraocular (eye) melanoma, Merkel cell cancer, etc.), hemangioma, malignant lymphoma (for example, reticulosarcoma, lymphosarcoma, Hodgkin's disease, etc.), melanoma (malignant melanoma), thyroid cancer (for example, medullary thyroid cancer, etc.), parathyroid cancer, nasal cancer, paranasal sinus cancer, bone tumor (for example, osteosarcoma, Ewing's tumor, uterine sarcoma, soft tissue sarcoma, etc.), metastatic medulloblastoma, angiofibroma, dermatofibrosarcoma protuberans, retinosarcoma, penis cancer, testicular tumor, pediatric solid tumor (for example, Wilms tumor, pediatric renal tumor, etc.), Kaposi's sarcoma, Kaposi's sarcoma caused by AIDS, maxillary sinus neoplasm, fibrous histiocytoma, leiomyosarcoma, rhabdomyosarcoma, chronic myeloproliferative disease, and leukemia (for example, acute myelogenous leukemia, acute lymphoblastic leukemia, etc.) may be exemplified and the target cancer is not limited thereto.

It has been reported that there is a specific gene expression/mutation pattern according to a cancer type including the cancer gene and cancer inhibiting gene described above. Therefore, when a biochip of the present embodiment is prepared on the basis of a gene expression profile for each cancer type and the like, it is possible to increase the accuracy of diagnosis.

In addition, when the biochip of the present embodiment is used, it is possible to predict the susceptibility/resistance of an anti-cancer agent. For example, it has been reported that, in the case of gefinitib which is an EGFR inhibitor, when EGFR in a test sample has an L858R mutation or G719X mutation, the mutation exhibits gefinitib susceptibility.

On the other hand, it has been reported that, when EGFR in a test sample has a T790M mutation and/or D761Y mutation, the mutation exhibits gefitinib resistance. In addition, it has been reported that these mutations exhibiting gefitinib resistance detected at a higher frequency as a stage of disease progresses. In the biochip of the present embodiment, since it is possible to easily quantify an EGRF gene exhibiting a resistance mutation, according to the biochip of the present embodiment, it is possible to check a degree of progress of cancer.

○ Influenza Virus Detection Biochip

In addition, in the biochip of the present embodiment, as the first affinity substance provided on the protective film, a nucleic acid complementary to a nucleic acid derived from influenza virus or a carbohydrate chain to which influenza virus specifically binds may be exemplified. That is, the biochip of the present embodiment may be a biochip for detecting influenza virus.

As the biochip of the present embodiment, for example, in A type, B type, and C type genomes, a nucleic acid that recognizes a certain mutation site including a reported mutation and is fixed to a protective film may be exemplified. In addition, as the first affinity substance, an antibody that can specifically recognize A type, B type and C type viruses may be used. In addition, it is known that influenza virus binds to a sialic acid residue when a cell is infected therewith, and since binding modes of a sialic acid to which virus can bind and a sugar differ according to a type of virus, as the first affinity substance, a sialic acid-containing carbohydrate chain to which A type, B type and C type viruses bind may be used.

Here, in this specification, "sialic acid" generally refers to a substance in which an amino group or a hydroxy group of a nine-carbon sugar neuraminic acid is substituted. For example, N-acetylneuraminic acid (Neu5Ac) acetylated in position 5 and N-glycolylneuraminic acid (Neu5Gc) modified with a glycolic acid may be exemplified.

According to the biochip of the present embodiment, it is possible to detect infection of influenza virus at an early stage.

In addition, when the biochip of the present embodiment is used over time, it is possible to perform follow-up observation of a disease state after viral infection.

INDUSTRIAL APPLICABILITY

According to the above embodiment, variation in GMR outputs is reduced, and it is possible to detect biomolecules in a sample with high accuracy and high sensitivity. In addition, when the biosensor of the present embodiment is used as a biochip, it is possible to perform diagnosis easily and rapidly, and it can be applied for, for example, cancer diagnosis, diagnosis for a specific type of cancer, diagnosis of a degree to which cancer has progressed, detection of influenza virus, identification of a type of influenza virus, and observation of a state of an influenza disease.

The invention claimed is:

1. A biosensor for detecting a biomolecule in a sample, the biosensor comprising:
a substrate having a surface in which a first region and a second region disposed adjacent to the first region are formed;
a magnetoresistance effect element that is disposed on the first region and is configured for a detected resistance value to be changed based on an input magnetic field;
a soft magnetic thin film that is disposed on the second region;
a protective film that is disposed on both the first region and the second region, covers a surface of the soft magnetic thin film, and is disposed on the top part of the second region and contains an affinity substance capable of recognizing the biomolecule on the outer surface of the second region exclusively; and
an MR cover film that is disposed on at least the top part of the first region and is disposed on the protective film above the magnetoresistance effect element, and is substantially free of the affinity substance,
wherein the soft magnetic thin film is configured to transmit a component in the in-plane direction of the laminate of a stray magnetic field of magnetic beads accumulated on the soft magnetic thin film to the magnetoresistance effect element,
the protective film and the MR cover film are made of different materials,
the protective film is composed of a plurality of films, and
the MR cover film is disposed on either of the first region and the second region on a film other than the top film among the plurality of films constituting the protective film.

2. The biosensor according to claim 1, further comprising a substance that reduces nonspecific adsorption of the biomolecules onto the outer surface of the MR cover film.

3. The biosensor according to claim 1,
wherein a material constituting the protective film is a noble metal and a material constituting the MR cover film is an oxide.

4. The biosensor according to claim 1,
wherein a material constituting the protective film is an oxide and a material constituting the MR cover film is a noble metal.

5. The biosensor according to claim 3,
wherein the noble metal is at least one selected from the group consisting of gold, silver, platinum, rhodium, ruthenium and palladium.

6. The biosensor according to claim 3,
wherein the oxide is at least one selected from the group consisting of alumina, silica, titanium oxide, zirconium oxide, indium oxide, tantalum oxide, zinc oxide, gallium oxide and tin oxide.

7. A biochip comprising the biosensor according to claim 1.

8. The biosensor according to claim 2,
wherein a material constituting the protective film is a noble metal and a material constituting the MR cover film is an oxide.

9. The biosensor according to claim 2,
wherein a material constituting the protective film is an oxide and a material constituting the MR cover film is a noble metal.

10. The biosensor according to claim 4,
wherein the noble metal is at least one selected from the group consisting of gold, silver, platinum, rhodium, ruthenium and palladium.

11. The biosensor according to claim 9,
wherein the noble metal is at least one selected from the group consisting of gold, silver, platinum, rhodium, ruthenium and palladium.

12. The biosensor according to claim 4,
wherein the oxide is at least one selected from the group consisting of alumina, silica, titanium oxide, zirconium oxide, indium oxide, tantalum oxide, zinc oxide, gallium oxide and tin oxide.

13. The biosensor according to claim 9,
wherein the oxide is at least one selected from the group consisting of alumina, silica, titanium oxide, zirconium oxide, indium oxide, tantalum oxide, zinc oxide, gallium oxide and tin oxide.

14. The biosensor according to claim 9,
wherein the substance that reduces nonspecific adsorption is at least one selected from the group consisting of a thiol group, an isothiocyanate group and a disulfide group.

15. The biosensor according to claim 8,
wherein the substance that reduces nonspecific adsorption has at least one of an alkoxysilane group and a phosphonic acid group.

16. A biosensor for detecting a biomolecule in a sample, the biosensor comprising:
a substrate having a surface in which a first region and a second region disposed adjacent to the first region are formed;
a magnetoresistance effect element that is disposed on the first region and is configured for a detected resistance value to be changed based on an input magnetic field;
a soft magnetic thin film that is disposed on the second region;
a protective film that is disposed on both the first region and the second region, covers a surface of the soft magnetic thin film, and is disposed on the top part of the second region and contains an affinity substance capable of recognizing the biomolecule on the outer surface of the second region exclusively; and
an MR cover film that is disposed on at least the top part of the first region and is disposed on the protective film above the magnetoresistance effect element, and is substantially free of the affinity substance,
wherein the soft magnetic thin film is configured to transmit a component in the in-plane direction of the laminate of a stray magnetic field of magnetic beads accumulated on the soft magnetic thin film to the magnetoresistance effect element,
the protective film and the MR cover film are made of different materials,
the protective film is composed of a plurality of films, and
the MR cover film is disposed only on the first region on a film other than the top film among the plurality of films constituting the protective film.

* * * * *